United States Patent
Lu et al.

(10) Patent No.: US 11,800,978 B2
(45) Date of Patent: Oct. 31, 2023

(54) DEEP LEARNING BASED ISOCENTER POSITIONING AND FULLY AUTOMATED CARDIAC MR EXAM PLANNING

(71) Applicant: Siemens Healthcare GmbH, Erlangen (DE)

(72) Inventors: Xiaoguang Lu, West Windsor, NJ (US); Carmel Hayes, Munich (DE)

(73) Assignee: Siemens Healthcare GmbH, Erlangen (DE)

( * ) Notice: Subject to any disclaimer, the term of this patent is extended or adjusted under 35 U.S.C. 154(b) by 1137 days.

(21) Appl. No.: 15/641,534

(22) Filed: Jul. 5, 2017

(65) Prior Publication Data
US 2018/0035892 A1 Feb. 8, 2018

Related U.S. Application Data

(60) Provisional application No. 62/371,281, filed on Aug. 5, 2016.

(51) Int. Cl.
| | | |
|---|---|---|
| *A61B 5/00* | (2006.01) | |
| *A61B 5/055* | (2006.01) | |
| *G06N 20/00* | (2019.01) | |
| *G06N 3/08* | (2023.01) | |
| *G06N 3/045* | (2023.01) | |

(52) U.S. Cl.
CPC .......... *A61B 5/0044* (2013.01); *A61B 5/0037* (2013.01); *A61B 5/055* (2013.01); *G06N 3/045* (2023.01); *G06N 3/08* (2013.01); *G06N 20/00* (2019.01)

(58) Field of Classification Search
CPC ..... A61B 5/0044; A61B 5/0037; A61B 5/055; A61B 5/004; A61B 5/0042; G06N 20/00; G06N 3/0454; G06N 3/08; G06T 2207/20081; G06T 2207/20084; G06T 2207/30048
See application file for complete search history.

(56) References Cited

U.S. PATENT DOCUMENTS

| | | | |
|---|---|---|---|
| 6,023,635 A * | 2/2000 | Liu | G01R 33/4835 324/307 |
| 6,708,055 B2 * | 3/2004 | Geiser | G06T 7/0012 600/425 |
| 2002/0095085 A1 * | 7/2002 | Saranathan | A61B 5/055 600/413 |

(Continued)

OTHER PUBLICATIONS

Milletari, Fausto. "Fully Convolutional Neural Networks for Volumetric Medical Image Segmentation". arXiv.org Jun. 15, 2016, pp. 1-11, arXiv:1606.04797 [cs.CV] (Year: 2016).*

(Continued)

*Primary Examiner* — Boniface Ngathi
*Assistant Examiner* — Milton Truong

(57) ABSTRACT

A computer-implemented method of performing deep learning based isocenter positioning includes acquiring a plurality of slabs covering an anatomical area of interest that comprises a patient's heart. For each slab, one or more deep learning models are used to determine a likelihood score for the slab indicating a probability that the slab includes at least a portion of the patient's heart. A center position of the patient's heart may then be determined based on the likelihood scores determined for the plurality of slabs.

20 Claims, 5 Drawing Sheets

(56) References Cited

U.S. PATENT DOCUMENTS

| | | | | |
|---|---|---|---|---|
| 2007/0081702 | A1* | 4/2007 | Porat | G06T 7/12 |
| | | | | 382/128 |
| 2013/0096414 | A1* | 4/2013 | Lu | A61B 5/0044 |
| | | | | 600/410 |
| 2015/0065803 | A1* | 3/2015 | Douglas | A61B 1/00009 |
| | | | | 600/200 |
| 2015/0133769 | A1* | 5/2015 | Laulicht | A61K 49/10 |
| | | | | 600/420 |
| 2018/0089530 | A1* | 3/2018 | Liu | G06K 9/4628 |

OTHER PUBLICATIONS

O. Emad, I. A. Yassine and A. S. Fahmy, "Automatic localization of the left ventricle in cardiac MRI images using deep learning," 2015 37th Annual International Conference of the IEEE Engineering in Medicine and Biology Society (EMBC), Milan, 2015, pp. 683-686 (Year: 2015).*

Lu, Xiaoguang, et al. Automatic view planning for cardiac MRI acquisition. Medical Image Computing and Computer-Assisted Intervention MICCAI 2011. Springer Berlin Heidelberg, 2011. 479-486.

Nitta, S., et al; (2013). Automatic slice alignment method for cardiac magnetic resonance imaging. Magnetic Resonance Materials in Physics, Biology and Medicine, 26(5), 451-461.

A. Krizhevsky et al. "ImageNet Classification with Deep Convolutional Neural Networks," Proc. NIPS, 2012.

* cited by examiner

DEEP LEARNING BASED ISOCENTER POSITIONING AND FULLY AUTOMATED CARDIAC MR EXAM PLANNING

CROSS-REFERENCE TO RELATED APPLICATIONS

This application claims the benefit of U.S. Provisional Application Ser. No. 62/371,281 filed Aug. 5, 2016, which is incorporated herein by reference in its entirety.

TECHNICAL FIELD

The present disclosure relates generally to methods, systems, and apparatuses for deep learning based isocenter positioning and fully automated cardiac exam planning for Magnetic Resonance Imaging (MRI) applications.

BACKGROUND

Magnetic Resonance Imaging (MRI) of the heart typically involves the acquisition of standard views aligned with the heart axes. Time-efficient and reproducible planning requires expertise in heart geometry and anatomy. One of the very first steps in cardiac MRI (CMRI) is to ensure that the heart is at the isocenter of the magnet. This requires the technician to identify the heart location from a few (e.g., three) localizer images obtained in standard orientations such as coronal views. With automated isocenter positioning and view planning, CMRI view planning can be streamlined without manual interventions. However, heart location and appearance in the initial, limited number of localizer images vary greatly, depending on the scouting image plane positions and patient's anatomical characteristics. Automatically localizing the heart from these scouts remains an open challenge and an integrated fully automated CMRI planning is still being pursued. In conventional clinical practice, isocenter positioning still relies on technicians to manually inspect the localizer images to identify the heart location and adjust the table position.

SUMMARY

Embodiments of the present invention address and overcome one or more of the above shortcomings and drawbacks, by providing methods, systems, and apparatuses for deep learning based isocenter positioning and fully automated cardiac exam planning for Magnetic Resonance Imaging (MRI) applications.

According to some embodiments of the present invention, a computer-implemented method of performing deep learning based isocenter positioning includes acquiring a plurality of slabs covering an anatomical area of interest that comprises a patient's heart. For each slab, one or more deep learning models (e.g., convolutional neural networks) are used to determine a likelihood score for the slab indicating a probability that the slab includes at least a portion of the patient's heart. A center position of the patient's heart may then be determined based on the likelihood scores determined for the plurality of slabs. In one embodiment, the method further includes determining a bounding box surrounding the patient's heart based on the likelihood scores determined for the plurality of slabs.

In some embodiments of the aforementioned method, the slabs comprise a first group of slabs acquired in a column direction with respect to the anatomical area of interest and a second group of slabs acquired in a row direction with respect to the anatomical area of interest. The likelihood score for each of the first group may be determined using a first deep learning model trained using previously acquired slabs acquired in the column direction. Similarly, the likelihood score for each of the second group may be determined using a second deep learning model trained using previously acquired slabs acquired in the row direction.

In some embodiments of the aforementioned method, the likelihood score for the slab comprises a plurality of likelihood data values. Each likelihood data value indicates a probability that a particular location within the slab includes the patient's heart. In one embodiment, the center position associated with the patient's heart is determined by first identifying a cluster of values within the plurality of likelihood data values and then determining a range of locations within the slab corresponding to the cluster. The median location within the range of locations is then designated as the center position of the heart. Prior to identifying the cluster of values, a predetermined threshold may be applied to the likelihood data values to (a) replace likelihood data values above the predetermined threshold with a maximum value and (b) replace likelihood data values below the predetermined threshold are specified as a minimum value.

Once the center position of the patient's heart is determined, it may be used in some embodiments for exam planning. For example, in one embodiment, a region of interest is defined based on the center position of the patient's heart. A stack of slices within the region of interest are acquired and used to reconstruct a 3D volume of the patient's heart. A left ventricle (LV) is segmented from the 3D MRI volume to yield a segmented LV. Then, a scan prescription for cardiac MRI acquisition can be automatically generated based on cardiac anchor points provided by the segmented LV in the 3D MRI volume.

According to another aspect of the present invention, as described in some embodiments, a system for performing deep learning based isocenter positioning includes an MRI scanner and one or more computers. The MRI scanner is configured to acquire a plurality of 3D volumes covering an anatomical area of interest that comprises a patient's heart. These 3D volumes may include multiple groups of 3D volumes, with each group being acquired in a different direction with respect to the anatomical area of interest. The computers are configured to perform an isocenter positioning process which includes using one or more deep learning models to determine a likelihood score for each 3D volume indicating a probability that the 3D volume includes at least a portion of the patient's heart. The computer can then determine a center position of the patient's heart based on the likelihood scores determined for the plurality of 3D volumes. Techniques similar to those described above with respect to the method of performing deep learning based isocenter positioning may be similarly applied to the aforementioned system.

According to other embodiments of the present invention, a method for performing deep learning based isocenter positioning includes generating a plurality of 3D volumes covering an anatomical area of interest that comprises a patient's heart based on a plurality of 2D scout images. Next, for each 3D volume, one or more deep learning models are used to determine a likelihood score for the 3D volume indicating a probability that the 3D volume includes at least a portion of the patient's heart. Then, a center position of the patient's heart is determined based on the likelihood scores determined for the plurality of 3D volumes.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there are shown in the drawings embodiments that are presently preferred, it being understood, however, that the invention is not limited to the specific instrumentalities disclosed. Included in the drawings are the following Figures.

DETAILED DESCRIPTION

The following disclosure describes the present invention according to several embodiments directed at deep learning based isocenter positioning and fully automated cardiac exam planning for Magnetic Resonance Imaging (MRI) applications. Briefly, a machine learning based approach is used to localize the heart from a few image scouts; then the localization information is used in a fully automated cardiac MRI (CMRI) planning method and system. In contrast to conventional machine learning-based approaches that use pre-defined image features that are hand-crafted by an algorithm designer, the techniques presented herein offer a purely data-driven approach using deep learning. Additionally, instead of typical patch-based scanning in learning-based approaches, the techniques described herein use a directional slab scanning scheme where image features are automatically learned to suit the task of finding the heart in scouts.

Conventional machine learning based approach may require pre-defined (hand-crafted) image features that the algorithm designer considers to be relevant to the task, and which may not be accurate. Instead, recent developments in Deep Learning (DL) shows that an end-to-end learning system can learn task-specific image features through the annotation of large representative datasets in a fully automated fashion. The essence of DL is about learning multiple levels of representation and abstraction that help make sense of data such as images, sound, and text. In particular, convolutional neural networks (CNNs), one of the representative deep learning architectures, have become powerful tools in a broad range of computer vision tasks. CNNs are machine-learning models that represent mid-level and high-level abstractions obtained from raw data (e.g., images). Various investigations indicate that the generic descriptors extracted from CNNs are effective in object recognition and localization in natural images. Recent development to leverage modern and customized GPUs makes DL based algorithms highly practical.

In typical learning-based image processing workflows, a patch-based scanning scheme is adopted. Each patch (i.e., sub-image) is evaluated by scanning through the entire image. Thus, for an image of size m by n, the number of patches/model-evaluations is in the order of $O(m*n)$.

Figure 1:
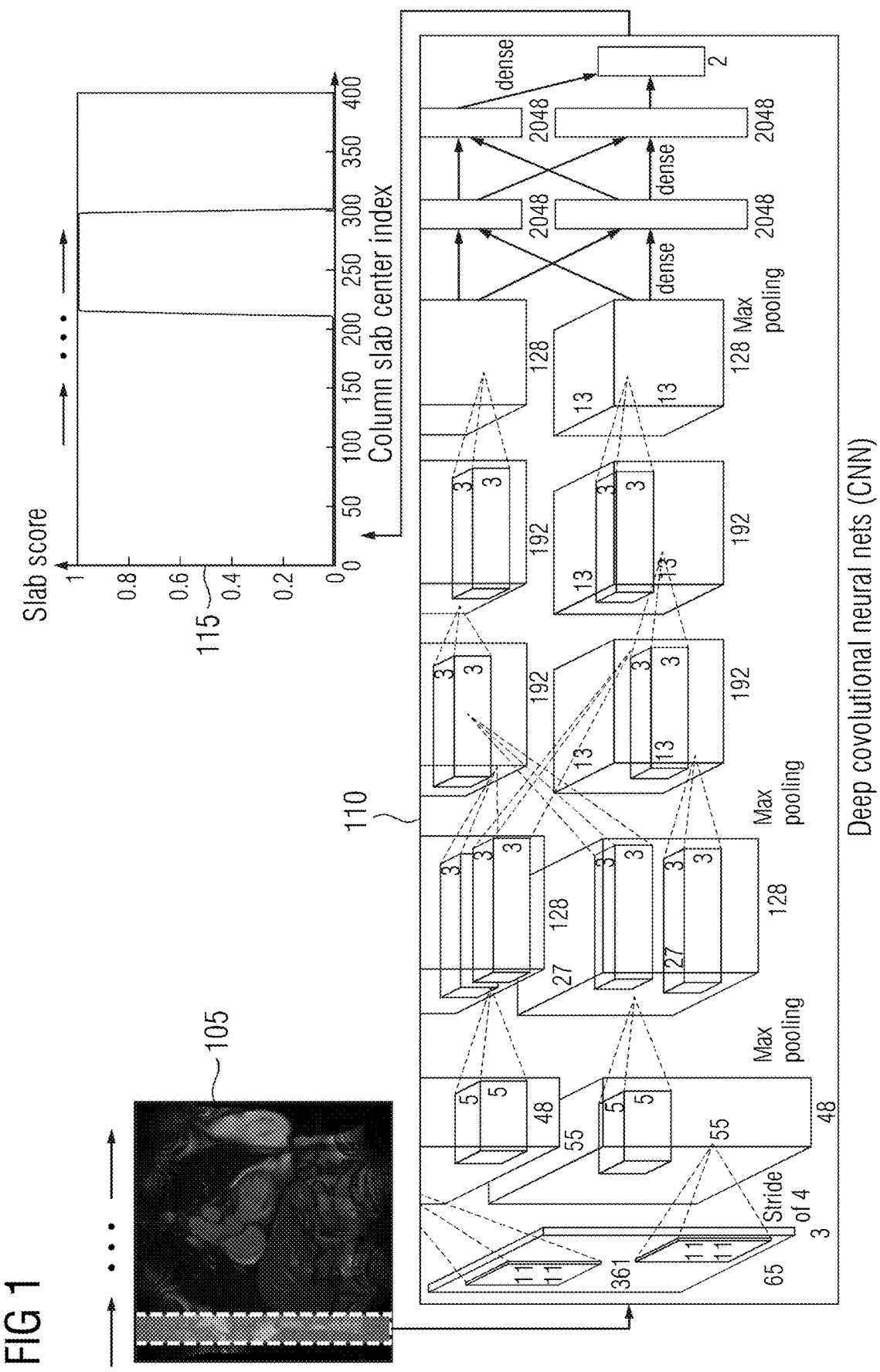
FIG. 1 provides an illustration of deep learning based isocenter positioning, as it may be applied in some embodiments.

FIG. 1 provides an illustration of deep learning based isocenter positioning, as it may be applied in some embodiments. The example shown in FIG. 1 is a slab-based scheme where each slab 105 (shown in dotted white) is a measurement volume that is fed into a deep learning network 110 to calculate likelihood of containing the heart. In some embodiments, the output of the deep learning network is a likelihood vs column position curve. For example plot 115 shows the likelihood that the heart is present (shown along the y-axis) for a plurality of column positions (shown along the axis). For row slabs (not show in FIG. 1), a similar plot may be generated for each row position. The total slabs/model-evaluations are in the order of $O(m+n)$. Once the likelihood along row/column is obtained at each row/column position, cluster analysis is applied jointly along row and column to determine the heart location in the scout. A convolutional neural network architecture is shown in FIG. 1 for illustration purposes; however, in principle, other similar deep learning networks can be utilized. It should also be noted that other acquisitions schemes may be utilized rather than the row/column technique described above. For example, although some accuracy would be lost, a slab-based scheme which uses only row slabs or only column slabs may be utilized with an appropriately-trained deep learning network.

Figure 2:
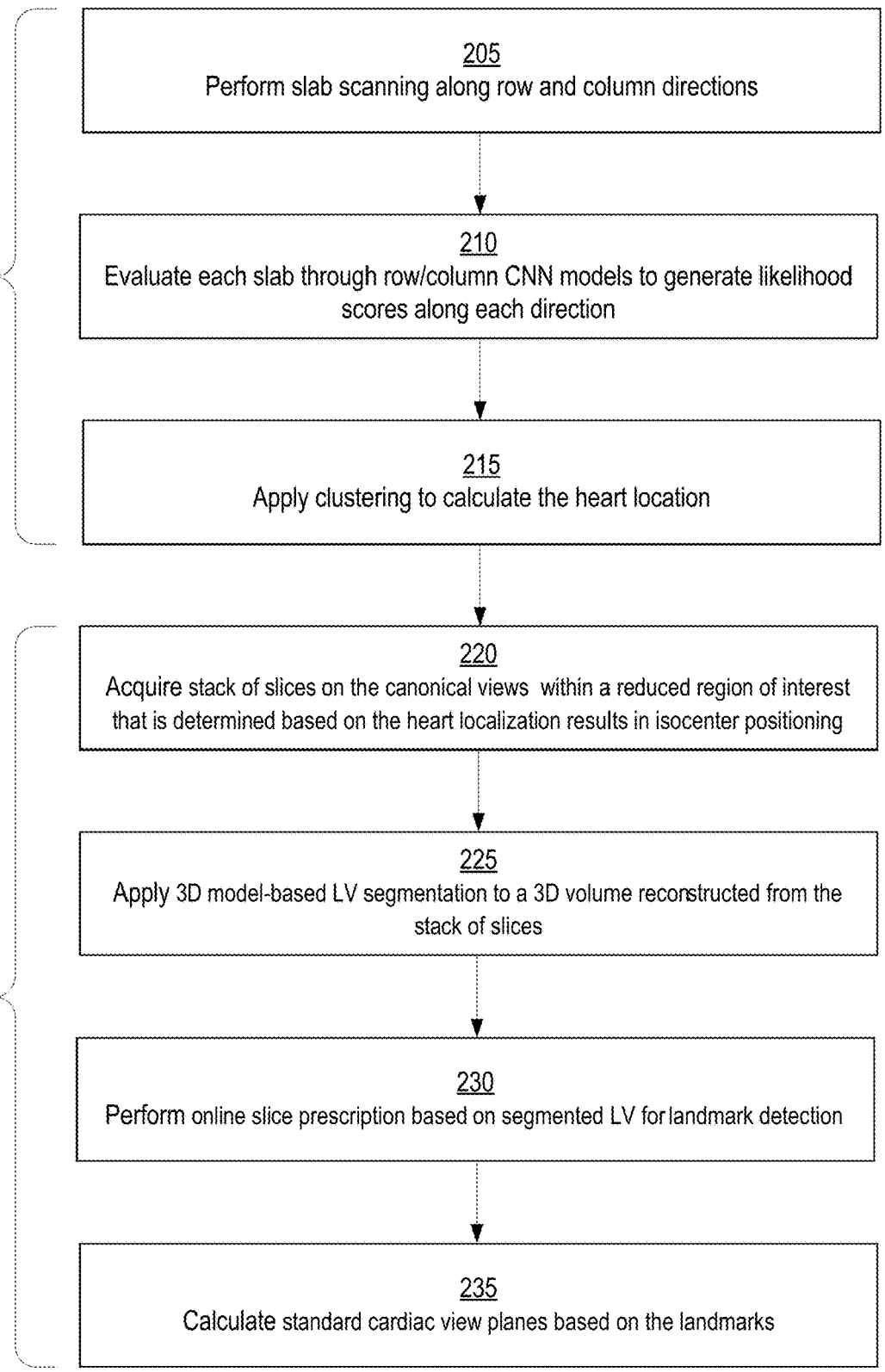
FIG. 2 illustrates a method for deep learning based isocenter positioning and fully automated cardiac MR exam planning, according to some embodiments.

FIG. 2 illustrates a method 200 for deep learning based isocenter positioning and fully automated cardiac MR exam planning, according to some embodiments. This method 200 can be performed, for example, using the MRI system 400 and the parallel processing memory architecture 500 shown in FIGS. 4 and 5, respectively, and described in further detail below. An isocenter positioning workflow is performed at steps 205-215. Initially, at step 205, slab scanning is performed along row and column directions. The term "slab" refers to a three-dimensional region of anatomical area being interest. Thus, the anatomical area can be understood as being divided into a plurality of slabs. To acquire data in the row direction, vertical slabs of the anatomical area are acquired, and to acquire data in the column data horizontal slabs of the anatomical area are acquired. Combined, the horizontal and vertical slabs serve to provide a grid of data which can be used for heart localization, as described below. Notably, the acquisition of the slabs may be done independently of one another and, in some embodiments, the acquisitions may be parallelized.

Next, at step 210, each slab acquired at step 205 is evaluated through row and column deep learning models to generate likelihood scores along each direction. These deep learning models (e.g., a CNN) are trained based on annotated images of slabs acquired from a large population of patients. In some embodiments, the annotation provided for each slab is a simple binary value indicating whether or not the heart is present. In other embodiments, more detailed information may be provided such as the exact center position of the heart within the slab.

In some embodiments, a bounding box enclosing the heart may be provided in the annotation information. When the bounding box is present in the annotation data, it can be used for training. For example, if an example slab overlaps with the bounding box, the slab can be considered a "positive" example with respect to the presence of the heart. Conversely, if there is no overlap, then the slab may be considered a "negative" example. The positive and negative examples are then used to train the deep learning models to generate a score for a new slab indicating the probability that the slab includes the heart (i.e., the new slab intersects with the bounding box containing the heart.)

At step 215, clustering is applied to the likelihood scores generated for each slab to determine the heart location. To illustrate the clustering process, consider the plot of likelihood scores 115 shown in FIG. 1. The "cluster" is between column positions 220 and 300 in this example. The heart position can then be determined by calculating the center point of the cluster (i.e., position 260). Note that, for the example shown in FIG. 1, thresholding was applied to ensure that each score was 0 and 1 (i.e., all scores above a predetermined threshold were set to 1, while scores below the predetermined threshold are set to 0). However, thresholding is not necessarily required and, in other embodiments, different techniques may be used for analyzing the likelihood curves and finding their center. Additionally, in some embodiments, additional filtering may be applied to the output of the models before clustering to ensure that a smooth curve is available for analysis.

Note that the plot of likelihood scores 115 shown in FIG. 1 only contains a single cluster (i.e., between column positions 220 and 300). If the results of the deep learning model show multiple clusters, then the one with the most column positions may be selected as the cluster used for further processing. For example, the plot of likelihood scores 115 included a cluster between column positions 100 and 150, along with the cluster between column positions 220 and 300, the latter cluster would be selected because it receives/presents larger total heart response than the former cluster.

Continuing with reference to FIG. 2, at steps 220-235, a fully automated planning scheme is performed. It should be noted that the particular technique shown in FIG. 2 is one example of an automatic view planning technique for cardiac magnetic resonance imaging acquisition and, in other embodiments, other view planning techniques generally known in the art may be used in conjunction with the isocenter positioning workflow described above.

Starting at step 220, a stack of slices on the canonical views (transverse or coronal) are acquired within a reduced region of interest that is determined based on the heart localization results in isocenter positioning. Next, at step 225, 3D model-based left ventricle (LV) segmentation is applied to a 3D volume reconstructed from the stack of slices. At step 230, online slice prescription is performed based on segmented LV for landmark detection. Then, at step 235, the landmarks are used to calculate standard cardiac view planes which are, in turn, provided to subsequent imaging steps for use as a basis for diagnostic scans.

Examples techniques for implementing steps 225-235 are described in detail in U.S. Pat. No. 8,948,484 to Lu et al., issued Feb. 3, 2015, and entitled "Method and system for automatic view planning for cardiac magnetic resonance imaging acquisition" ("Lu"), the entirety of which is incorporated herein by reference. For example, in some embodiments of the present invention (and further explained in Lu), a LV is segmented in the 3D MRI volume, and a scan prescription for cardiac MRI acquisition is automatically generated based on cardiac anchor points provided by the segmented LV in the 3D MRI volume. A 3-chamber view scanning plane can be determined based on the cardiac anchor points provided by the segmented LV. Landmarks can be detected in a mid-ventricular short axis slice reconstructed from the 3D MRI volume and corresponding to a short axis slice prescribed in the short axis stack, and a 2-chamber view scanning plane and a 4-chamber view scanning plane can be determined based on the landmarks detected in the reconstructed mid-ventricular short axis slice together with the landmark(s) inherent in the segmented LV such as apex.

Although isocenter positioning is described in FIGS. 1 and 2 with respect to 2D scout images, it should be noted that the general technique can be extended to 3D images as well. In embodiments where 3D images are used, the volumes used for positioning comprise a first group of 3D volumes acquired in a first direction with respect to an anatomical area of interest and a second group of 3D volumes acquired in a second direction with respect to the anatomical area of interest. Then, the likelihood score used of locating the heart in each volume in the first group is determined using a first deep learning model trained using previously acquired 3D volumes acquired in the first direction. Similarly, the likelihood score for each volume in the second group is determined using a second deep learning model trained using previously acquired 3D volumes acquired in the second direction. In some embodiments, rather than acquiring the 3D volumes directly, the 3D volumes are generated based on a plurality of 2D scout images.

Additionally, although the techniques described above with respect to FIGS. 1 and 2 focus on the left ventricle, these techniques are not limited as such and may be extended to other portions of cardiac anatomy. For example, if models of the entire heart and great vessels are available, automatic planning may be performed on the right ventricle, the atria, the great vessels—aorta, pulmonary artery, etc.

Figure 3:
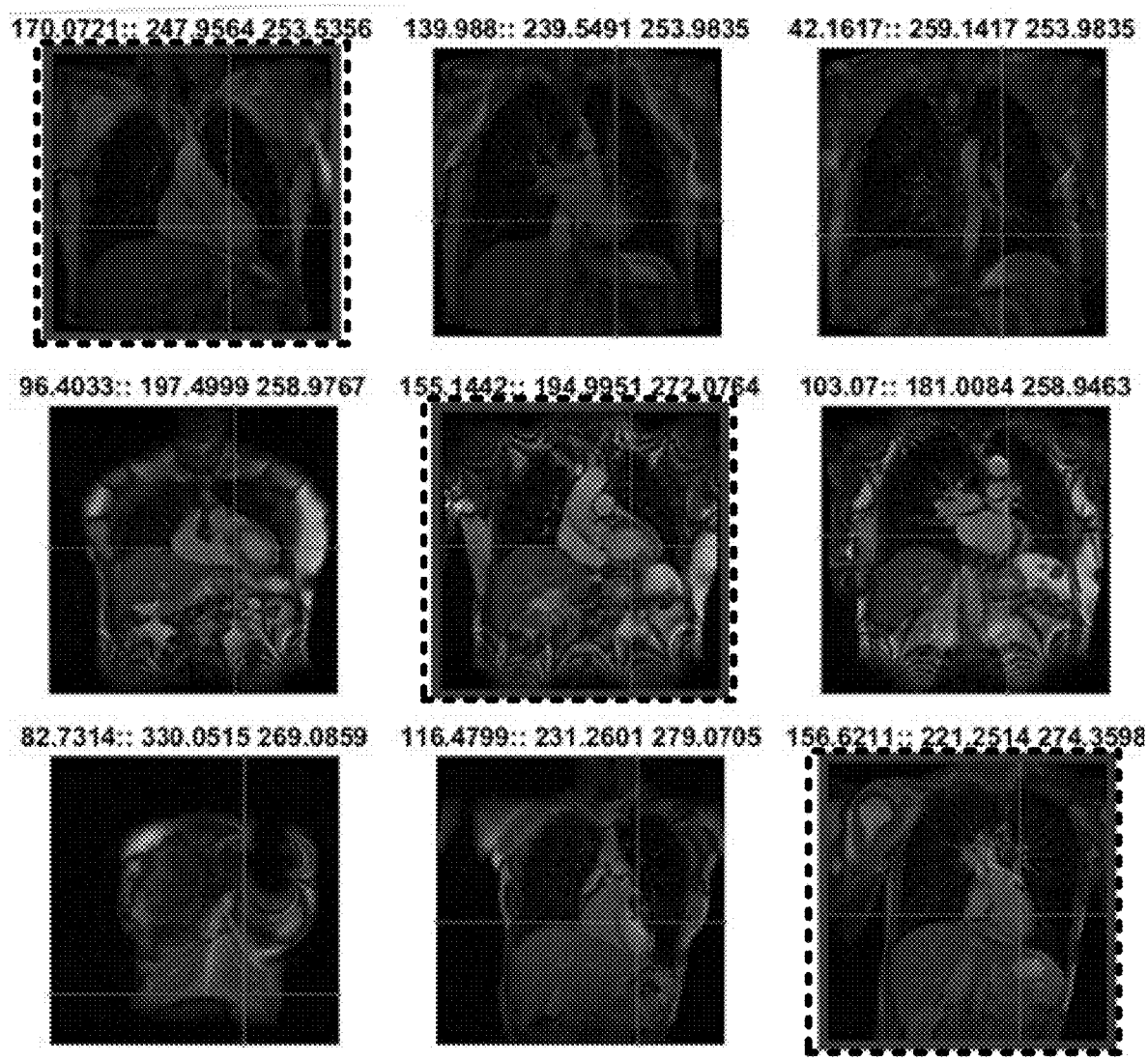
FIG. 3 shows example cases of automatic heart localization from coronal scouts, as may be acquired in some embodiments.

FIG. 3 shows example cases of automatic heart localization from coronal scouts. Each row presents three coronal scouts. Three numbers on top of each figure are [a:b c], where a for likelihood, b and c for automatically detected heart row index and column index, respectively. The dotted line boxes indicate the scout with the highest localization confidence by the deep learning model for each case.

Figure 4:
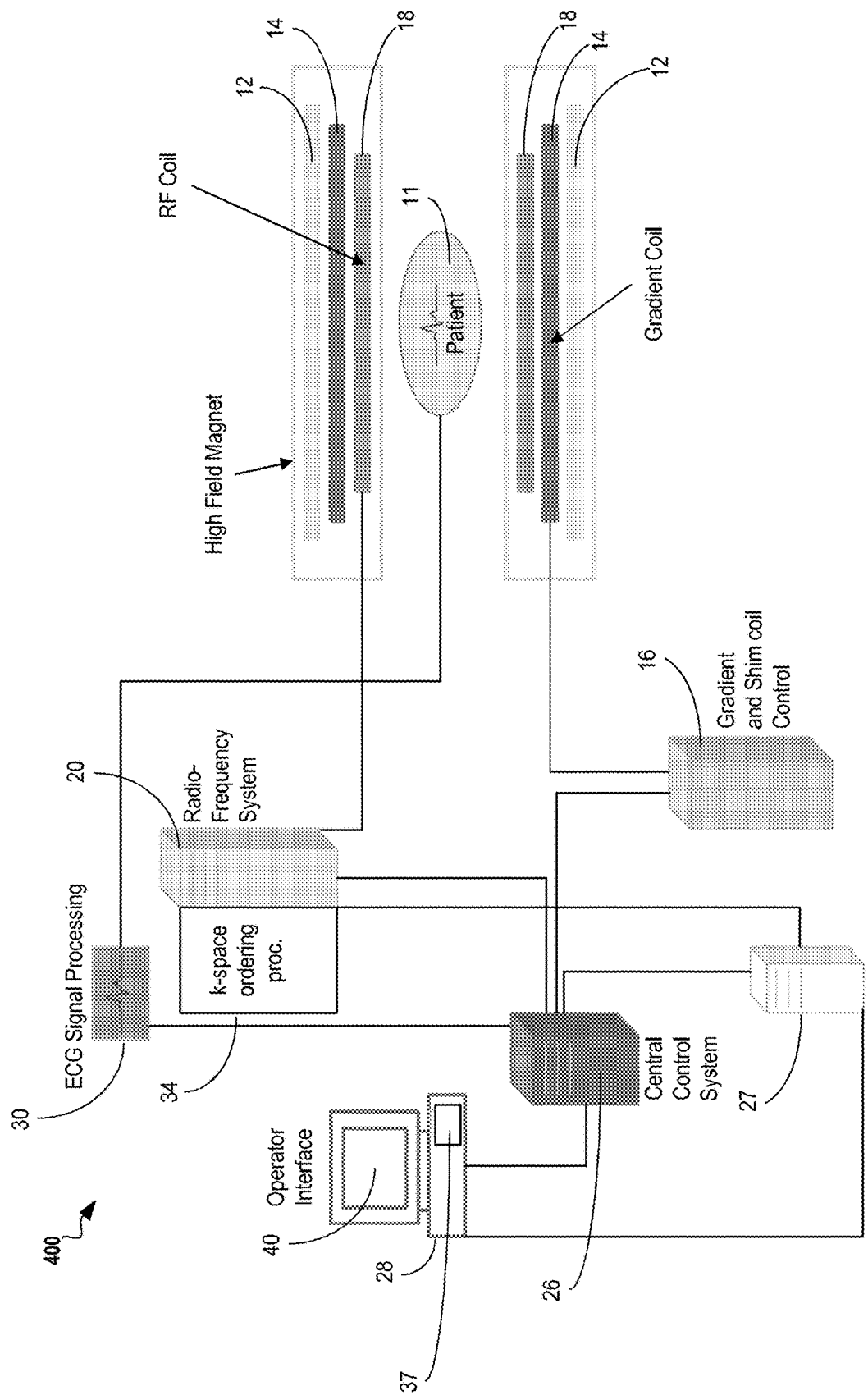
FIG. 4 shows an example MRI system which may be used to perform slab scanning and acquire stacks of slices, according to some embodiments.

FIG. 4 shows an example MRI system 400 which may be used to perform slab scanning and acquire stacks of slices, according to some embodiments. This system 400 orders the acquisition of frequency domain components representing MRI data for storage in a k-space storage array. In system 400, magnetic coils 12 create a static base magnetic field in the body of patient 11 to be imaged and positioned on a table. Within the magnet system are gradient coils 14 for producing position dependent magnetic field gradients superimposed on the static magnetic field. Gradient coils 14, in response to gradient signals supplied thereto by a gradient and shim coil control module 16, produce position dependent and shimmed magnetic field gradients in three orthogonal directions and generate magnetic field pulse sequences. The shimmed gradients compensate for inhomogeneity and variability in an MRI device magnetic field resulting from patient anatomical variation and other sources. The magnetic field gradients include a slice-selection gradient magnetic field, a phase-encoding gradient magnetic field and a readout gradient magnetic field that are applied to patient 11.

Further radio frequency (RF) module 20 provides RF pulse signals to RF coil 18, which in response produces magnetic field pulses which rotate the spins of the protons in the imaged body of the patient 11 by 90 degrees or by 180 degrees for so-called "spin echo" imaging, or by angles less than or equal to 90 degrees for so-called "gradient echo" imaging. Gradient and shim coil control module 16 in conjunction with RF module 20, as directed by central control unit 26, control slice-selection, phase-encoding, readout gradient magnetic fields, radio frequency transmission, and magnetic resonance signal detection, to acquire magnetic resonance signals representing planar slices of patient 11.

In response to applied RF pulse signals, the RF coil 18 receives magnetic resonance signals, i.e., signals from the excited protons within the body as they return to an equilibrium position established by the static and gradient magnetic fields. The magnetic resonance signals are detected and processed by a detector within RF module 20 and k-space component processor unit 34 to provide a magnetic resonance dataset to an image data processor for processing into an image. In some embodiments, the image data processor is located in central control unit 26. However, in other embodiments such as the one depicted in FIG. 3, the image data processor is located in a separate unit 27. Electrocardiogram (ECG) synchronization signal generator 30 provides ECG signals used for pulse sequence and imaging synchronization. A two or three dimensional k-space storage array of individual data elements in k-space component processor unit 34 stores corresponding individual frequency components comprising a magnetic resonance dataset. The k-space array of individual data elements has a designated center and individual data elements individually have a radius to the designated center.

A magnetic field generator (comprising coils 12, 14, and 18) generates a magnetic field for use in acquiring multiple individual frequency components corresponding to individual data elements in the storage array. The individual frequency components are successively acquired in an order in which the radius of respective corresponding individual data elements increases and decreases along a substantially spiral path as the multiple individual frequency components are sequentially acquired during acquisition of a magnetic resonance dataset representing a magnetic resonance image. A storage processor in the k-space component processor unit 34 stores individual frequency components acquired using the magnetic field in corresponding individual data elements in the array. The radius of respective corresponding individual data elements alternately increases and decreases as multiple sequential individual frequency components are acquired. The magnetic field acquires individual frequency components in an order corresponding to a sequence of substantially adjacent individual data elements in the array and magnetic field gradient change between successively acquired frequency components which is substantially minimized.

Central control unit 26 uses information stored in an internal database to process the detected magnetic resonance signals in a coordinated manner to generate high quality images of a selected slice(s) of the body (e.g., using the image data processor) and adjusts other parameters of system 400. The stored information comprises predetermined pulse sequence and magnetic field gradient and strength data as well as data indicating timing, orientation and spatial volume of gradient magnetic fields to be applied in imaging. Generated images are presented on display 40 of the operator interface. Computer 28 of the operator interface includes a graphical user interface (GUI) enabling user interaction with central control unit 26 and enables user modification of magnetic resonance imaging signals in substantially real time. Continuing with reference to FIG. 4, display processor 37 processes the magnetic resonance signals to reconstruct one or more images for presentation on display 40, for example. Various techniques may be used for reconstruction. For example, in conventional systems, an optimization algorithm is applied to iteratively solve a cost function which results in the reconstructed image.

Figure 5:
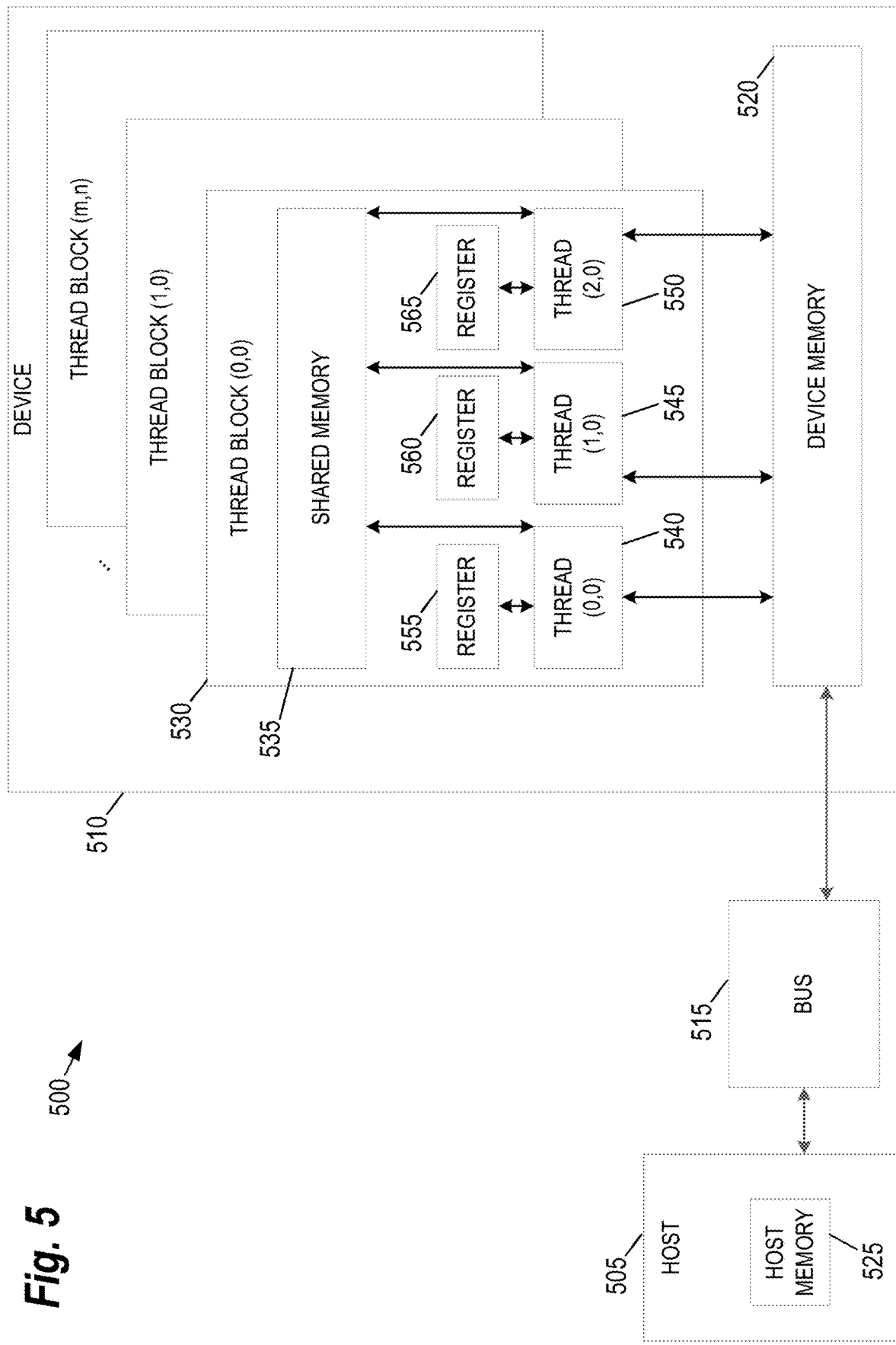
FIG. 5 provides an example of a parallel processing memory architecture that may be utilized in some embodiments.

FIG. 5 provides an example of a parallel processing memory architecture 500 that may be utilized in some embodiments of the present invention. For example, this architecture 500 may be used for performing calculations related to the deep learning networks discussed above with respect to FIGS. 1 and 2, as well as other general processing related to the techniques described herein. This architecture 500 may be used in embodiments of the present invention where NVIDIA™ CUDA (or a similar parallel computing platform) is used. The architecture includes a host computing unit ("host") 505 and a graphics processing unit (GPU) device ("device") 510 connected via a bus 515 (e.g., a PCIe bus). The host 505 includes the central processing unit, or "CPU" (not shown in FIG. 5) and host memory 525 accessible to the CPU. The device 510 includes the GPU and its associated memory 520, referred to herein as device memory. The device memory 520 may include various types of memory, each optimized for different memory usages. For example, in some embodiments, the device memory includes global memory, constant memory, and texture memory.

Parallel portions of a deep learning application may be executed on the architecture 500 as "device kernels" or simply "kernels." A kernel comprises parameterized code configured to perform a particular function. The parallel computing platform is configured to execute these kernels in an optimal manner across the architecture 500 based on parameters, settings, and other selections provided by the user. Additionally, in some embodiments, the parallel computing platform may include additional functionality to allow for automatic processing of kernels in an optimal manner with minimal input provided by the user.

The processing required for each kernel is performed by grid of thread blocks (described in greater detail below). Using concurrent kernel execution, streams, and synchronization with lightweight events, the architecture 500 of FIG. 5 (or similar architectures) may be used to parallelize training of a deep neural network. For example, in some embodiments, a separate kernel is dedicated to determining a likelihood score for each column or row slab.

The device 510 includes one or more thread blocks 530 which represent the computation unit of the device 510. The term thread block refers to a group of threads that can cooperate via shared memory and synchronize their execution to coordinate memory accesses. For example, in FIG. 5, threads 540, 545 and 550 operate in thread block 530 and access shared memory 535. Depending on the parallel computing platform used, thread blocks may be organized in a grid structure. A computation or series of computations may then be mapped onto this grid. For example, in embodiments utilizing CUDA, computations may be mapped on one-, two-, or three-dimensional grids. Each grid contains multiple thread blocks, and each thread block contains multiple threads. For example, in FIG. 5, the thread blocks 530 are organized in a two dimensional grid structure with m+1 rows and n+1 columns. Generally, threads in different thread blocks of the same grid cannot communicate or synchronize with each other. However, thread blocks in the same grid can run on the same multiprocessor within the GPU at the same time. The number of threads in each thread block may be limited by hardware or software constraints. In some embodiments, the individual thread blocks can be selected and configured to optimize training of the deep learning network. For example, in one embodiment, each thread block is assigned a subset of training data with overlapping values. In other embodiments, thread blocks can be dedicated to different vertebral sections included in the spine.

Continuing with reference to FIG. 5, registers 555, 560, and 565 represent the fast memory available to thread block 530. Each register is only accessible by a single thread. Thus, for example, register 555 may only be accessed by thread 540. Conversely, shared memory is allocated per thread block, so all threads in the block have access to the same shared memory. Thus, shared memory 535 is designed to be accessed, in parallel, by each thread 540, 545, and 550 in thread block 530. Threads can access data in shared memory 535 loaded from device memory 520 by other threads within the same thread block (e.g., thread block 530). The device memory 520 is accessed by all blocks of the grid and may be implemented using, for example, Dynamic Random-Access Memory (DRAM).

Each thread can have one or more levels of memory access. For example, in the architecture 500 of FIG. 5, each thread may have three levels of memory access. First, each thread 540, 545, 550, can read and write to its corresponding registers 555, 560, and 565. Registers provide the fastest memory access to threads because there are no synchronization issues and the register is generally located close to a multiprocessor executing the thread. Second, each thread 540, 545, 550 in thread block 530, may read and write data to the shared memory 535 corresponding to that block 530. Generally, the time required for a thread to access shared memory exceeds that of register access due to the need to synchronize access among all the threads in the thread block. However, like the registers in the thread block, the shared memory is typically located close to the multiprocessor executing the threads. The third level of memory access allows all threads on the device 510 to read and/or write to the device memory. Device memory requires the longest time to access because access must be synchronized across the thread blocks operating on the device. Thus, in some embodiments, the processing of each slab is coded such that it primarily utilizes registers and shared memory and only utilizes device memory as necessary to move data in and out of a thread block.

The embodiments of the present disclosure may be implemented with any combination of hardware and software. For example, aside from parallel processing architecture presented in FIG. 5, standard computing platforms (e.g., servers, desktop computer, etc.) may be specially configured to perform the techniques discussed herein. In addition, the embodiments of the present disclosure may be included in an article of manufacture (e.g., one or more computer program products) having, for example, computer-readable, non-transitory media. The media may have embodied therein computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

The invention claimed is:

1. A computer-implemented method of performing deep learning based isocenter positioning, the method comprising:
    acquiring a plurality of slabs covering an anatomical area of interest that comprises a patient's heart, including slabs oriented in a column direction and in a row direction;
    for each slab in the column and row direction, using one or more deep learning models to determine a plurality of likelihood scores for the slab, each of the plurality of likelihood scores indicating a probability that the slab includes at least a portion of the patient's heart, wherein the one or more deep learning models were trained based on annotated images of patients' anatomy to output the plurality of likelihood scores;
    determining a reduced region of interest that is a subset of the anatomical area by finding a center position of a cluster of the plurality of probability scores for the plurality of slabs that corresponds to the patient's heart;
    acquiring a stack of slices in canonical directions in the reduced region of interest based on the determining step; and
    calculating cardiac view planes for diagnostic imaging based on landmarks within the stack of slices.

2. The method of claim 1, wherein the plurality of slabs comprise a first group of slabs acquired in a column direction with respect to the anatomical area of interest and a second group of slabs acquired in a row direction with respect to the anatomical area of interest.

3. The method of claim 2,
wherein the likelihood score for each of the first group of slabs is determined using a first deep learning model trained using previously acquired slabs acquired in the column direction, and
wherein the likelihood score for each of the second group of slabs is determined using a second deep learning model trained using previously acquired slabs acquired in the row direction.

4. The method of claim 1, wherein the likelihood score for the slab comprises a plurality of likelihood data values, each likelihood data value indicating a probability that a particular location within the slab includes the patient's heart.

5. The method of claim 4, further comprising:
identifying a cluster of values within the plurality of likelihood data values;
identifying a range of locations within the slab corresponding to the cluster of values;
identifying the center position associated with the patient's heart using a median location within the range of locations.

6. The method of claim 5, further comprising:
prior to identifying the cluster of values, applying a predetermined threshold to the plurality of likelihood data values to (a) replace likelihood data values above the predetermined threshold with a maximum value and (b) replace likelihood data values below the predetermined threshold that are specified as a minimum value.

7. The method of claim 1, further comprising:
determining a bounding box surrounding the patient's heart based on the likelihood scores determined for the plurality of slabs.

8. The method of claim 1, wherein the one or more deep learning models comprise a convolutional neural network.

9. The method of claim 1, further comprising:
reconstructing a 3D Magnetic Resonance Imaging (MM) volume of the patient's heart based on the stack of slices;
segmenting a left ventricle (LV) in the 3D MRI volume to yield a segmented LV; and
automatically generating a scan prescription for cardiac MRI acquisition based on cardiac anchor points provided by the segmented LV in the 3D MRI volume.

10. A system for performing deep learning based isocenter positioning, the system comprising:
an MRI scanner configured to acquire a plurality of 3D volumes covering an anatomical area of interest that comprises a patient's heart, each 3D volume including slabs oriented in a column direction and in a row direction;
one or more computers configured to perform an isocenter positioning process comprising:
for each 3D volume, using one or more deep learning models to determine a plurality of likelihood scores for the 3D volume indicating a probability that the 3D volume includes at least a portion of the patient's heart, wherein the one or more deep learning models were trained based on annotated images of patients' anatomy to output the plurality of likelihood scores;
determining a reduced region of interest that is a subset of the anatomical area by finding a center position of a cluster of the plurality of probability scores for the plurality of 3D volumes that corresponds to the patient's heart;
acquiring a stack of slices in canonical directions in the reduced region of interest based on the determining step; and
calculating cardiac view planes for diagnostic imaging based on landmarks within the stack of slices.

11. The system of claim 10, wherein the plurality of 3D volumes comprise a first group of 3D volumes acquired in a first direction with respect to the anatomical area of interest and a second group of 3D volumes acquired in a second direction with respect to the anatomical area of interest.

12. The system of claim 11,
wherein the likelihood score for each of the first group of 3D volumes is determined using a first deep learning model trained using previously acquired 3D volumes acquired in the first direction, and
wherein the likelihood score for each of the second group of 3D volumes is determined using a second deep learning model trained using previously acquired 3D volumes acquired in the second direction.

13. The system of claim 10, wherein the likelihood score for the 3D volume comprises a plurality of likelihood data values, each likelihood data value indicating a probability that a particular location within the 3D volume includes the patient's heart.

14. The system of claim 13, wherein the isocenter positioning process further comprises:
identifying a cluster of values within the plurality of likelihood data values;
identifying a range of locations within the 3D volume corresponding to the cluster of values;
identifying the center position associated with the patient's heart using a median location within the range of locations.

15. The system of claim 14, wherein the isocenter positioning process further comprises:
prior to identifying the cluster of values, applying a predetermined threshold to the plurality of likelihood data values to (a) replace likelihood data values above the predetermined threshold with a maximum value and (b) replace likelihood data values below the predetermined threshold are specified as a minimum value.

16. The system of claim 10, wherein the isocenter positioning process further comprises:
determining a bounding box surrounding the patient's heart based on the likelihood scores determined for the plurality of 3D volumes.

17. The system of claim 10, wherein the one or more deep learning models comprise a convolutional neural network.

18. The system of claim 10, wherein the one or more computers comprise a parallel computing platform which applies the one or more deep learning models to multiple 3D volumes in parallel to determine likelihood score for the 3D volume indicating the probability that the 3D volume includes at least a portion of the patient's heart.

19. The system of claim 10, wherein the isocenter positioning process further comprises:
reconstructing a 3D MRI volume of the patient's heart based on the stack of slices;
segmenting a left ventricle (LV) in the 3D MRI volume to yield a segmented LV; and
automatically generating a scan prescription for cardiac MRI acquisition based on cardiac anchor points provided by the segmented LV in the 3D MRI volume.

20. A method for performing deep learning based isocenter positioning, the method comprising:
generating a plurality of 3D volumes covering an anatomical area of interest that comprises the patient's heart based on a plurality of 2D scout images, each 3D volume including slabs oriented in a column direction and in a row direction;

for each 3D volume, using one or more deep learning models to determine a plurality of likelihood scores for the 3D volume indicating a probability that the 3D volume includes at least a portion of the patient's heart, wherein the one or more deep learning models were trained based on annotated images of patients' anatomy to output the plurality of likelihood scores;

determining a reduced region of interest that is a subset of the anatomical area by finding a center position of a cluster of the plurality of probability scores for the plurality of 3D volumes that corresponds to the patient's heart;

acquiring a stack of slices in canonical directions in the reduced region of interest based on the determining step; and calculating cardiac view planes for diagnostic imaging based on landmarks within the stack of slices.

* * * * *